(12) United States Patent
Müller et al.

(10) Patent No.: US 12,364,447 B2
(45) Date of Patent: Jul. 22, 2025

(54) CONTROL SYSTEM FOR A MEDICAL INSTALLATION AND MEDICAL INSTALLATION

(71) Applicant: Siemens Healthcare GmbH, Erlangen (DE)

(72) Inventors: Matthias Müller, Bamberg (DE); Thomas Pfeiffer, Adelsdorf (DE); Franz Atzinger, Nuremberg (DE); Harald Karl, Fuerth (DE); Claus-Günter Schliermann, Kemnath (DE); Franz Dirauf, Bad Staffelstein (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 179 days.

(21) Appl. No.: 18/307,942

(22) Filed: Apr. 27, 2023

(65) Prior Publication Data

US 2024/0074720 A1    Mar. 7, 2024

(30) Foreign Application Priority Data

Apr. 29, 2022    (DE) ...................... 10 2022 204 210.7

(51) Int. Cl.
| | |
|---|---|
| *A61B 6/00* | (2024.01) |
| *A61B 6/04* | (2006.01) |
| *A61B 6/10* | (2006.01) |
| *A61B 6/46* | (2024.01) |

(52) U.S. Cl.
CPC ............ *A61B 6/102* (2013.01); *A61B 6/0487* (2020.08); *A61B 6/4476* (2013.01); *A61B 6/467* (2013.01); *A61B 6/54* (2013.01)

(58) Field of Classification Search
CPC ........... A61B 6/102; A61B 6/10; A61B 6/547; A61B 6/4464; A61B 6/4476; A61B 1/00042
See application file for complete search history.

(56) References Cited

U.S. PATENT DOCUMENTS

| 11,980,487 B2 * | 5/2024 | Deinlein ................ A61B 6/547 |
|---|---|---|
| 2020/0405408 A1 | 12/2020 | Shelton, IV et al. |
| 2022/0114069 A1 | 4/2022 | Alben et al. |

* cited by examiner

*Primary Examiner* — Don K Wong
(74) *Attorney, Agent, or Firm* — Harness, Dickey & Pierce, P.L.C.

(57) ABSTRACT

A control system for a medical installation, wherein the control system is configured to control a motorized movement of an installation component. The control system includes a control path and a protection path. The control path is configured to control the motorized movement. The protection path is independent of the control path and configured to monitor the control path with regard to compliance with a safety criterion for the motorized movement. The protection path includes at least one freely programmable microcontroller.

20 Claims, 2 Drawing Sheets

CONTROL SYSTEM FOR A MEDICAL INSTALLATION AND MEDICAL INSTALLATION

CROSS-REFERENCE TO RELATED APPLICATION(S)

The present application claims priority under 35 U.S.C. § 119 to German Patent Application No. 10 2022 204 210.7, filed Apr. 29, 2022, the entire contents of which are incorporated herein by reference.

FIELD

One or more example embodiments of the present invention relate to a control system for a medical installation for controlling a motorized movement of a movable installation component. The control system comprises a functional control path and a safety-related protection path. The protection path comprises at least one freely programmable microcontroller.

BACKGROUND

If medical installations for imaging or therapy and/or individual components thereof are moved by motorized mechanisms, collisions may occur between people in the vicinity of the medical installation, i.e., users or patients, and the installation or the moving component. This poses a high risk of injury but also of damage.

To reduce the risk, motorized movements are typically implemented via a dead man's release, i.e., the movement can only be executed as long as the user holds down a release button (also referred to as dead man's switch, dead man's grip, DMG). If the user releases the release button, an emergency stop of the movement of the installation or components is automatically initiated, for example.

This means that the task of monitoring the movement lies with the user. The user must ensure that collisions are avoided by permanent visual monitoring of the movement of the device.

It is also known that the user can be relieved via a tactile collision facility. Tactile collision facilities use tactile sensor systems in parallel with monitoring by the user to detect whether a collision is taking place and, if a collision event is detected, initiate an emergency stop, even if the release button is actuated. Therefore, in the event of a collision occurring despite permanent monitoring, the tactile collision facilities ensure that movement is stopped.

A collision facility typically has one or more tactile sensors that are mainly arranged in areas of the device with an increased risk of collision. These are, for example, nipping points and/or areas that are difficult for the operator to see. For example, these areas are hidden from the user by other parts of the installation and so the user must assume a certain position relative to the medical installation in order to reach the release button.

Even in the event of unexpected, in particular erroneous, movements of the medical installation, for example in the case of unauthorized high speeds, incorrect directions of movement or the like, a tactile collision facility can initiate a protective measure more quickly than a user, because the user generally requires a longer reaction time than an automatic system.

These well-known, rather simple safety principles (dead man's release, tactile collision facility) can be implemented with discrete hardware logic. However, attention and monitoring by the user cannot be dispensed with in such cases. In addition, when the collision facility is used, a collision always occurs first.

Therefore, modern safety concepts aim to ensure operational safety or movement safety by other technical solutions and, in particular, to free users from monitoring tasks. Overall, not least in view of the ever-increasing shortage of personnel in medical care, novel solutions are required to enable extensively autonomous device movements in order to optimize workflow in medical facilities and thereby increase the attractiveness of the device.

Autonomous device movements are in high demand, particularly in the field of mobile applications; for example, mobile C-arms, mobile and flexible X-ray detector carts or mobile computed tomography scanners are gaining in importance for operators of medical facilities. Such devices can be moved not only within one room, but also flexibly in a plurality of different rooms within the medical facility. Autonomous movements of individual components also have a high economic and practical benefit in stationary installations, in particular if positioning of the component takes a long time and thus occupies a large proportion of the time needed to examine or treat the patient.

The sensor systems already available today, which are able to precisely determine a location, position and/or orientation of a patient or user or component of the medical installation or the like could enable completely autonomous component positioning. However, this would require a system for automatically maintaining safety standards that are mandatory for installations and devices used in medical technology and are standardized accordingly.

As mentioned in the introduction, known discrete hardware logic can only be used for simple safety functions, for example an emergency stop. In addition, discrete hardware logic does not enable manual or visual monitoring to be dispensed with. An emergency stop in which the medical installation is put into idle mode always interrupts current examination/treatment. This must then be actively restarted or sometimes even repeated.

Advanced safety concepts can implement alternative safety functions that first provide further safety measures before initiating an ultimate emergency stop. Advanced safety concepts are also embodied to be preventive, i.e., they are embodied to initiate further safety measures before collision occurs.

Consequently, advanced safety concepts offer a wider range of different safety functions but, to implement them, they require increased flexibility in the acquisition and intelligent processing of sensor data or system data in order, in terms of risk reduction, to act in accordance with approval requirements for compliance with the first-failure safety of the medical installation.

Advanced safety concepts can already be implemented with programmable safety logic. This entails industry-standard control apparatuses by which different safety functions can be programmed and implemented. However, commercially available programmable safety logic is always linked to physical control hardware, for example in the form of standard control modules from a respective supplier. Standard control modules in each case offer limited flexibility in terms of data interfaces and programming options. In the sense of a modular system, therefore, a plurality of safety functions can be implemented via a suitable selection of standard control modules. If the safety system is highly complex, the available standardized safety logics rapidly increase the number and complexity of the required components and the overall costs. Typically, the standard solutions require a plurality of printed circuit boards.

In addition, available standard solutions for programmable safety logic tend to be aimed at industrial fields of application, for example for manufacturing. Thus, in case of doubt, medical device-specific safety functions and interfaces cannot be covered or cannot be covered completely.

SUMMARY

Against the above-discussed background, it is an object of one or more example embodiments of the present invention to provide alternative means and/or mechanisms that allow improved implementation of a complex safety concept for a medical installation. In particular, it is an object of one or more example embodiments of the present invention to enable the implementation of a large number of different programmable safety functions. In particular, it is a further object of one or more example embodiments of the present invention to provide easily integrable, and thus flexibly usable, means and/or mechanisms for the implementation of a complex safety concept with cost neutrality and low expenditure on components.

At least this object is achieved by a control system for a medical installation for controlling a motorized movement of an installation component and/or the medical installation and a corresponding medical installation. Preferred and/or alternative advantageous embodiment variants are the subject matter of the dependent claims.

Therefore, one or more example embodiments of the present invention relate to a control system for a medical installation for controlling a motorized movement of an installation component and/or the medical installation.

One or more example embodiments of the present invention furthermore relate to a corresponding medical installation with a control system according to example embodiments of the present invention.

The control system is embodied to control a movement of an installation component or the entire medical installation.

In some embodiments, a medical installation is embodied as a medical imaging installation, intervention installation or treatment installation. A medical imaging installation serves to generate image data relating to a patient's anatomy. Herein, a medical imaging installation implements at least one type of physical imaging technology. The medical imaging installation can be embodied as an X-ray imaging installation or as a magnetic resonance imaging installation, as an ultrasound device or the like. It can also comprise other imaging methods. An intervention installation serves the purpose of performing a medical or surgical intervention on a patient. It is in particular possible to use medical or surgical instruments that are mechanically guided, moved or actuated or the like for this purpose. In particular, the medical instrument can be arranged on a movable robotic arm. The intervention installation can be used for the purpose of examinations, therapy or treatment. A treatment installation is used to treat a patient. In particular, a treatment installation can be embodied as a radiation therapy installation, wherein, for example, it uses X-rays or particle radiation.

A first aspect of the medical installation according to embodiments of the present invention relate to an installation embodied as a radiography installation comprising two movable installation components in the form of an X-ray tube stand and a patient bench. Radiography refers to conventional fluoroscopic X-ray imaging in which generally two-dimensional X-ray images of the patient are generated.

The medical installation comprises at least two movable installation components. Consequently, it is also possible for it to comprise more than two movable installation components.

In some embodiments of the present invention, an installation component is a subunit of the medical installation that can be adjusted or moved relative to at least one other installation component. An installation component is, for example, a robotic arm that carries a medical intervention instrument. In one embodiment of the present invention, an installation component is embodied as an X-ray tube stand that is embodied to be floor-mounted or ceiling-mounted or can be movably connected to other installation components. In one embodiment of the present invention, a second installation component is embodied as a patient bench or more precisely, as a table top of a patient bench, wherein the table top is used to support or receive or position the patient and can be adjusted relative to a table superstructure. In some embodiments of the present invention, the table superstructure of the patient bench can also be embodied to be adjustable relative to other installation components in the sense of a movable installation component.

The movable installation component can also be embodied as an X-ray detector stand. The above information relating to the X-ray tube stand also applies in this case.

A further aspect of embodiments of the present invention is directed at a medical installation embodied as a mobile medical X-ray imaging installation. Here, the entire medical installation is the movable installation component, which, in this case, can be moved relative to or in the surroundings. For example, the medical installation can be embodied to be movable in a translatory manner by a rail guide system; in another embodiment, the mobile installation has roller or castor elements with which the mobile installation moves over a substrate, in particular with directional adaptation. In particular, in some embodiments, the mobile installation is embodied with an omnidirectional chassis.

The mobile medical X-ray imaging installation can further comprise at least one movable installation component. The above explanations relating to the installation component apply accordingly.

In some embodiments of the present invention, movement of the movable installation components serves, for example, to position the imaging components relative to one another or relative to the patient anatomy. For example, movement of both the patient bench (including the patient) and the X-ray tube via the stand can be provided to arrange a body region to be mapped in the isocenter or beam path of a medical installation.

Otherwise, movement serves to (re)position a medical installation in an examination or treatment setting. For example, the installation can be moved between two examination rooms in a medical facility, between a resting position, charging station, cleaning station and location of use.

Movement of an installation component is preferably embodied as a translatory movement; rotational movement is also possible. In some embodiments of the present invention, the movement is a combination or concatenation of a plurality of individual movements. The movement of the installation component can comprise a movement along or about one or more spatial axes.

To execute a movement in the sense of embodiments of the present invention, the medical installation according to embodiments of the present invention also comprises at least one drive unit. The drive unit comprises at least one motorized drive. The drive unit can also be embodied as a drive unit of an installation component. In one embodiment of the present invention, the medical installation can also comprise a plurality of drive units depending on the number of movable installation components. The at least one motorized drive is embodied to effect a translatory or rotational movement along or about a spatial axis. In a preferred embodiment, a drive unit comprises a large number of motorized drives, in particular a motorized drive for each degree of freedom or each axis of movement. In this way, in some embodiments, many different travel or adjustment paths can be implemented if a plurality of motorized drives are used together, simultaneously or in succession.

In a preferred embodiment, a motorized drive is embodied as an electromotive linear or rotary drive. In preferred embodiments, the motorized drive is embodied as a servomotor, which is characterized by high power and can therefore implement a fully automatic adjustment movement, even if the movable installation component has a high deadweight. In addition, a servomotor has a sensor system implemented as standard for acquiring a location or position parameter, a currently effective motor torque or the force exerted. This sensor system can advantageously be used in a component-efficient and cost-efficient manner by the system according to embodiments of the present invention for controlling movement in order to acquire at least one of said parameters. In other embodiments, the drive unit comprises a lower power motorized auxiliary drive for at least one degree of freedom. This is embodied to provide motorized support for a manual adjustment movement. This adjustment movement is implemented by manual and motorized force input.

The control system according to embodiments of the present invention for controlling a movement of an installation component comprises a control path for controlling the motorized movement. The control path comprises a plurality of control components. Together, these form the functional part of the movement control for the installation. This means that the control path comprises all control components required to effect automated motorized movement of the installation component or the installation.

In addition, the control system also comprises a protection path independent of the control path. The protection path is embodied to monitor the control path with regard to compliance with a safety criterion, preferably a plurality of different safety criteria, for the motorized movement. In particular, an individual and specific safety criterion is defined and stored for each degree of freedom or each axis of movement. Herein, the at least one safety criterion is in particular defined as a first-failure safety criterion. This ensures compliance with first-failure safety for the motorized movement.

First-failure safety defines and standardizes system properties or installation properties with regard to operational safety. These must be fulfilled in order for a medical installation to be certified as first-failure-safe for product approval.

First-failure safety can be described as follows.
  A first random hardware failure can occur at any time and at any place in the medical installation.
  This first failure shall not represent an unnecessary unacceptable risk.
  If the first failure is obvious to the user, the medical installation shall not be used any further.
  If the first failure cannot be detected, it is assumed that a second failure will occur after a predefined time (MOFT—multiple fault tolerance time).
  The combination of the first and second failure shall not cause any hazard to people or machines.

The safety criterion used to detect a first failure can preferably be monitoring of a fault tolerance time (FTT) or a (spatial) overshoot distance. Fault tolerance times or overshoot distances are specific to individual movement axes, the type of movement and/or the respective installation component and, in some embodiments of the present invention, form the at least one safety criterion for which compliance must be ensured by the protection path. Consequently, the protection path comprises at least one control component set up to monitor at least one safety criterion and, in the event of non-compliance with the safety criterion, for example if the fault tolerance time is overshot, to initiate a transfer of the medical installation into a safe state. In a preferred embodiment, the protection path, in particular the at least one control component of the protection path, can be embodied to generate at least one control signal, in particular for the drive unit, in order to bring the medical installation into the safe state. The control signal can, for example, be directed at stopping or slowing down a movement of an installation component or bringing about a change in the direction of movement.

A further aspect of embodiments of the present invention is directed at a control system in which the safety criterion is at least one criterion from the following group:
  minimum distance between movable installation component and/or the medical installation,
  a maximum speed of movement,
  a maximum acceleration,
  maximum torque,
  maximum force,
  a position boundary along a direction of movement.

A minimum distance in the sense of embodiments of the present invention describes a predefined safety distance between a movable installation component or medical installation and a moving and/or stationary object in the vicinity of the medical installation. The safety distance is advantageously selected such that a collision of the movable component with the object can be reliably avoided, taking into account braking distances or braking times specific to a movable component and reaction times of the control system or the drive unit.

An object can in particular be a patient, an operator and/or a further movable component of the medical installation or any installation component.

Compliance with or non-overshooting of a maximum speed of movement, maximum acceleration or maximum torque or maximum force exerted by the drive unit on the movable installation component also result in a safe state of movement, in particular if the movable installation component is moved together with a patient, for example if the patient is located on a movable patient bench and/or the movement of the installation component takes place in close proximity to the patient.

A position boundary along a direction of movement or an axis of movement can also correspond to a safety criterion, for example if instability of the medical installation would result if the movable installation component were to overshoot the position boundary.

According to embodiments of the present invention, the protection path comprises at least one freely programmable microcontroller. Freely programmable in the sense of embodiments of the present invention means that the protection path or the at least one control component of the protection path per se has no hardware or software restrictions with regard to the number, embodiment and monitoring of possible safety criteria. Accordingly, the microcontroller is embodied to implement arbitrarily programmable computing operations for monitoring and compliance with the safety criteria which go well beyond discrete AND/OR computing operations.

For this purpose, according to a first aspect of embodiments of the present invention, the microcontroller comprises a plurality of digital and analog signal inputs and signal outputs, wherein at least one signal input is linked to at least one signal output via a programmable safety function.

The microcontroller is embodied to acquire input information via the signal inputs in the form of at least one of a plurality of different operating parameters, movement parameters, position parameters or surroundings parameters and/or user input.

An operating parameter can, for example, be a parameter that indicates whether the movable component is moving or at rest at a particular point in time.

A movement parameter can, for example, be a parameter that indicates the speed, acceleration and/or direction in which the movable component is moved at a particular point in time.

A position parameter can, for example, be a parameter that is embodied to indicate an absolute or relative location and/or position of the movable component at a particular point in time.

A surroundings parameter can, for example, be a parameter that indicates the state of the surroundings of the movable component at a particular point in time. The state of the surroundings can in particular indicate whether an object, for example a medical object or a person is located in the immediate vicinity of the movable component.

According to embodiments of the present invention, operation parameters, movement parameters, position parameters or surroundings parameters are acquired via operation sensors, movement sensors, position sensors and/or surroundings sensors that cooperate with the control system according to embodiments of the present invention or, in one embodiment of the present invention, are comprised by the control system. In some embodiments, at least one sensor can be embodied as a proximity sensor or collision sensor that is known per se in order to provide a surroundings parameter. At least one sensor can be embodied as a rotary encoder or location encoder that is known per se in order to provide position parameters or operation parameters. In one embodiment, at least one sensor can be embodied as a position sensor or distance sensor in order to provide an absolute or relative position or location via a position parameter or location parameter. At least one sensor can also be embodied as a distance sensor or proximity sensor or collision sensor that is known per se in order to provide a surroundings parameter.

In one embodiment of the present invention, at least one of the operation sensors, movement sensors, position sensors and/or surroundings sensors is connected to the control path and/or the protection path. In a preferred embodiment, at least one of the sensors is in each case connected to the protection path via a signal input of the microcontroller. In preferred embodiments, at least one of the aforementioned sensors is connected to both the protection path and the control path or embodied as part of the same. In other words, an acquired parameter can function as an input value of both the control path and the protection path.

A safety function according to embodiments of the present invention is freely programmable and, in this respect, can be optimally adapted to the specific application. In other words, the safety function can be adapted to installation-specific requirements, to the specific respective axis of movement of the movable installation component without it being necessary to adapt the control hardware.

The safety function describes a functional relationship between an input value in the form of at least one of the aforementioned parameters, a safety criterion and an output value. According to embodiments of the present invention, the output value is present as a control signal, which is output in each case via the linked signal output, for example to a control component of the control path. In some embodiments, the control signal can comprise an at least partially preprocessed intermediate result or an intermediate value, which is output to a control component of the control path for further processing and in particular for generating a control command in particular for the drive unit of the installation component. In an alternative embodiment, the control signal can also directly comprise a control command for the drive unit.

As mentioned in the introduction, a safety function links a signal input of the microcontroller of the protection path to a signal output. In some embodiments, a safety function can link a plurality of signal inputs to a signal output or vice versa, for example if a plurality of control components of the control path are involved for compliance with first-failure safety. In a further embodiment, it is also possible for a plurality of signal inputs to be linked to a plurality of signal outputs via a safety function.

Herein, according to embodiments of the present invention, each safety function is directed at the monitoring of a safety criterion for an axis of movement or a degree of freedom of movement.

The sum of all freely programmable safety functions implemented on the microcontroller of the protection path forms the safety logic according to embodiments of the present invention.

Accordingly, a further aspect of embodiments of the present invention is directed at a control system in which the programmable safety logic comprises at least one application-specific safety function for each link between the signal input and signal output for compliance with a safety criterion.

The signal inputs and signal outputs of the microcontroller of the protection path preferably comprise a plurality of standardized signal interfaces. For example, a plurality of safe digital signal inputs, safe digital signal outputs, safe analog signal inputs, in particular interfaces to surroundings sensors, movement sensors, position sensors or the like, for example rotary encoder interfaces, are provided.

The microcontroller of the protection path can furthermore comprise at least one, preferably more, communication interfaces, for example in the form of a UART or SPI interface, which comprise communication via a CAN bus, in particular for communication with at least one control component of the control path.

According to embodiments of the present invention, overall, 50 to 100 signal inputs and signal outputs are provided, preferably there are between 80 and 95 signal inputs and signal outputs. This results in enormous flexibility in the design of the safety logic, since the necessary signal inputs and signal outputs are provided, at least optionally, for any installation or application-specific safety function. This means that the safety logic to be implemented can be adapted to any medical installations or applications via the microcontroller thus enabling flexible use of the control system according to embodiments of the present invention. In particular in the case of complex safety logic of a medical installation, this enables the component complexity, which would otherwise have to be implemented with standard commercially available control components, to be significantly reduced. The reduced component complexity is furthermore reflected in the costs of the control system. The same microcontroller can be used for a plurality of medical installations. All that is required on the part of the manufacturer is an adaptation of the implemented safety logic.

Therefore, the inventors have recognized that the functionality of an independent protection path required to ensure first-failure safety can be executed particularly simply and conveniently in the form of a microcontroller or via a circuit macro.

According to a further aspect of embodiments of the present invention, the control path comprises a central control module, a motor control module and an interface module. The central control module is embodied to generate control signals for a drive unit of the medical installation, in particular for a motorized drive of at least one axis of movement of a movable installation component. The motor control module is embodied to control the drive unit according to the generated control signals. The interface module is embodied to acquire a surroundings parameter, an operation parameter, a movement parameter, a position parameter and/or a user input of the medical installation and, based thereon, to generate and transmit a control signal for the control module and/or the motor control module.

As already mentioned in the introduction, the control path forms the functional part of the control system for movement control for the medical installation. The control path per se is consequently embodied to trigger and/or to control and/or to terminate an automatic motorized movement of an installation component if all control components comprised are intact.

The interface module comprises at least one, preferably a plurality of data interfaces for acquiring surroundings parameters, operating parameters, movement parameters, position parameters and/or user input. Herein, the aforementioned parameters can be acquired by a sensor module of the medical installation comprising at least one surroundings sensor, one movement sensor or operation sensor or one position sensor and provided via the corresponding data interfaces. In some embodiments, the user input is acquired via an input unit or an operating element of the medical installation. The user input is preferably a haptic user input, the operating element is preferably embodied as a manually operated switch, button or lever, but a touch display is also possible here. Other forms of user input are also possible, for example the user input can be in the form of a gesture or speech. The input unit is then embodied to interpret human speech or a body movement and, based thereon, to derive a user intention and generate a corresponding input signal.

In some embodiments of the present invention, the user input represents an input signal corresponding to an operator request. The operator request is preferably a request for movement release or a request for an emergency stop, by which movement of the movable component is to be manually authorized, i.e., released, or terminated.

In some embodiments, the interface module is embodied to generate a control signal based on at least one of the above parameters and/or the user input. The control signal can be embodied in various ways. In some embodiments, the interface module can be embodied to directly generate a control command for at least one drive component of the drive unit as a control signal. In other embodiments, the interface module is embodied to convert the at least one parameter and/or the user input into a trigger signal for initiating a stored control rule, for example a specific safety function, into a status signal indicating a status of an installation or state of movement, an intermediate result for further processing or the like. In this respect, the interface module is embodied to further process the at least one parameter and/or the user input and transmit the same to the central control module and/or the motor control module via corresponding data interfaces. The further processing can comprise filtering, classification, threshold alignment or the like.

The central control module is also set up to generate control signals for one or all drive units of the medical installation. The central control module of the control path is embodied to generate control signals for the drive unit, in particular based on the control signals of the interface module. In this respect, the central control module is also embodied to further process incoming control signals from the interface module comprising status signals, trigger signals and/or intermediate results via implemented functional control logic.

The motor control module, also known as the motor controller, is embodied to convert the movement specifications comprised in the received control signals by correspondingly controlling various drive components or motor components. The motor control module is furthermore embodied in particular to control the operation of an electromotive drive in accordance with the control signal specifications.

The central control module, the interface module, and the motor control module can in each case have at least one or more computing units, for example in the form of processors. In particular, the central control module can be embodied as a submodule of the central computing facility of the medical installation or comprise parts thereof. In particular, the computing units integrated in the interface module, in the motor control module and in the central control module can be embodied in each case as a so-called "system-on-a-chip", (SoC) and in each case comprise parts or sections of the implemented functional movement control. In addition to the different data interfaces, the interface module preferably comprises a microcontroller embodied to further process the incoming aforementioned parameters and/or user inputs as described.

As mentioned above, a further aspect of the control system is directed at a control path which furthermore comprises a sensor module, wherein the sensor module comprises at least one surroundings sensor and/or one movement sensor, which is embodied to acquire a surroundings parameter and/or a movement parameter of the medical installation and to transmit the same to the interface module. In other words, in this embodiment, the interface module and the sensor module of the control system are in data communication. In one embodiment, the sensor module can further also comprise a position sensor or operation sensor and transmit the parameters acquired, as described above, to the interface module.

In a further embodiment, the interface module is further connected to the input unit of the medical installation via a corresponding data interface in order to acquire the user signal.

The interfaces or data interfaces for data exchange between the sensor module or the operator unit of the medical installation and the interface module and between the interface module, central control module and motor control module can in this respect be implemented in the form of at least one, preferably more, in particular preferably in the form of a plurality of different suitable individual data interfaces, which can have a hardware interface and/or software interface, a data bus, for example a PCI bus, a USB interface, a FireWire interface, a WLAN interface, ZigBee interface or a Bluetooth interface. In particular the interfaces to or from the control module are preferably embodied as interfaces to an SPI or UART bus. The individual data interface can be embodied as a cable-bound interface and/or wireless interface. It can be embodied for analog or digital data transmission.

In a further embodiment of the control system, the microcontroller of the protection path can also be in data communication with the sensor module via at least one, preferably more, of its signal inputs and acquire at least one of the aforementioned parameters as an input value for the implemented safety logic.

In one embodiment of the present invention, therefore, the parameters acquired and output by the surroundings sensors, movement sensors, operation sensors and/or position sensors can be used as input data both for the execution of the control logic and for the execution of the safety logic.

In a further aspect of the control system according to embodiments of the present invention, at least one signal input of the microcontroller of the protection path is connected to the input unit of the medical installation for acquiring a user input redundantly to the control path. Accordingly, the microcontroller of the protection path can be connected to the input unit of the medical installation via at least one of its signal inputs in order to acquire a user input via a redundant input signal representing an acquired user input parallel to the control path.

However, an alternative aspect of the control system comprises a protection path comprising at least one redundant surroundings sensor and/or redundant movement sensor, which is also embodied to acquire a surroundings parameter and/or a movement parameter of the medical installation and transmit the same to the microcontroller of the protection path. In particular, the drive unit of the movable component can comprise at least one of the following redundant sensors: position sensor, location encoder or rotary encoder, torque sensor or force sensor, which is in each case coupled to at least one signal input of the microcontroller of the protection path and provides at least one of the aforementioned parameters as an input value for the safety logic.

According to embodiments of the present invention, an operation sensor and/or position sensor can be embodied redundantly solely for acquiring and outputting parameters for the protection path. In this way, the propagation of a failure that has already occurred at sensor level can advantageously be avoided with increased hardware outlay in order to meet safety specifications even more fully.

A further aspect of the control system according to the embodiments of the present invention relate to the protection path in which the at least one freely programmable microcontroller is arranged as a standalone function block on the same printed circuit board as the interface module of the control path. In this embodiment, the hardware of the protection path is advantageously integrated into the already existing hardware of the control path. In this respect, in this embodiment according to the present invention, the microcontroller of the interface unit and the microcontroller of the protection path are arranged on the same PCB (printed circuit board).

Herein, the embodiment of the protection path microcontroller as a standalone function block should ensure that the execution of the safety logic of the protection path microcontroller does not depend on the functionality or individual computing or communication steps of the interface module microcontroller.

The standalone nature is in particular achieved by the provision of analog and/or digital signal inputs on the protection path microcontroller that allow the acquisition of surroundings parameters, operation parameters, movement parameters or position parameters or user input independent of the interface module.

In a particularly preferred embodiment, the central control module and/or the motor control module are arranged on the same printed circuit board. This advantageously enables the component complexity of the control system according to embodiments of the present invention to be further reduced.

According to a further preferred aspect of the control system, the protection path is embodied to communicate with the control path via at least one signal output and/or signal input of the microcontroller. In a preferred embodiment, the control path and protection path are connected via a plurality of signal inputs or signal outputs. Data exchange between the control path and microcontroller of the protection path serves to provide bidirectional feedback within the control process. On the one hand, the execution of the safety logic on the protection path microcontroller can depend on feedback signals from the control logic implemented in the control path. On the other hand, in some embodiments, it can be provided that the medical installation is brought into the safe state based on a control signal of the protection path microcontroller and that control components of the control path are interposed for this purpose. For example, according to embodiments of the present invention, the motor controller of the control path is often active based on a corresponding control signal of the protection path microcontroller.

In particular, the protection path microcontroller exchanges data with both the microcontroller of the interface module, and the motor controller via corresponding interfaces. In other embodiments, alternatively or additionally, there can be a direct connection between the signal output of the microcontroller of the protection path to the drive unit. For example, the protection path microcontroller can be directly connected to a braking facility of the drive unit in order to generate a control signal comprising an emergency stop command based on an acquired user input or an acquired surroundings parameter and send it to the braking facility. In this way, in some embodiments, the present invention enables movement to be stopped particularly quickly.

The signal inputs and signal outputs for communication between the protection path and control path can be embodied as described above.

A further aspect of the present invention is directed at a control system in which the microcontroller comprises a generic software module and an application-specific software module. The application-specific software module comprises or implements the plurality of application-specific safety functions for compliance with at least one safety criterion in each case. Herein, the safety criterion is specific to the respective movable component and/or the movement to be performed by the movable component. On the other hand, the generic software module is embodied to enable access to the application-specific software module and/or to perform application-specific safety test methods for individual signal inputs, signal outputs and/or application-specific safety functions of the microcontroller of the protection path.

The generic software module is embodied such that it does not require any knowledge or information about the respective application of the application-specific software module or the safety functions implemented thereon. This is implemented in that the safety test methods are in each case embodied generically for the standardized signal inputs and signal outputs. In the event of a safety test method for at least one of the signal inputs and signal outputs outputting a failure, in one embodiment of the present invention, the control path is informed accordingly via corresponding data interfaces by the microcontroller of the protection path and any motorized movement control by the control path is prevented until the safety test method has been executed without error. Accordingly, the safety test methods are embodied to be executed repeatedly, i.e., within for the respective signal input or signal output of the microcontroller. The time interval can be a few seconds, or even hours or days. In particular, the repetition can always take place when the control system according to embodiments of the present invention is restarted.

For example, the generic software module is embodied to check a safety test method for testing a signal input of the microcontroller connected to a surroundings sensor, in particular a collision sensor, in order to ensure that a collision of the movable component is detected correctly in each case. For this purpose, the generic software module can, for example, simulate a collision via voltages generated at the surroundings sensor input and monitor the surroundings parameters expected at the microcontroller signal input and compare them with target values. In addition, the generic software module is embodied also to test signal inputs of the microcontroller connected to the input unit of the medical installation, in particular the signal input connected to a movement release switch or handle of the medical installation, or the signal output connected to the motor control module for transmitting an emergency stop signal (STO—system torque offs) via a corresponding safety test method.

In some embodiments, the microcontroller comprises a watchdog that monitors the correct execution of the application-specific safety functions.

In this way, according to embodiments of the present invention, failures within the protection path are avoided or identified by permanent monitoring, not only of the safety-critical signal inputs and signal outputs of the microcontroller, but also of the individual safety functions per se for malfunctions.

BRIEF DESCRIPTION OF THE DRAWINGS

The above-described properties, features and advantages of embodiments of the present invention and the manner in which these are achieved will become clearer and more plainly comprehensible in conjunction with the following description of the exemplary embodiments explained in more detail in conjunction with the drawings. This description does not limit the present invention to these exemplary embodiments. In different figures, the same components are given the same reference symbols. The figures are not generally to scale. They show.

DETAILED DESCRIPTION

Figure 1:
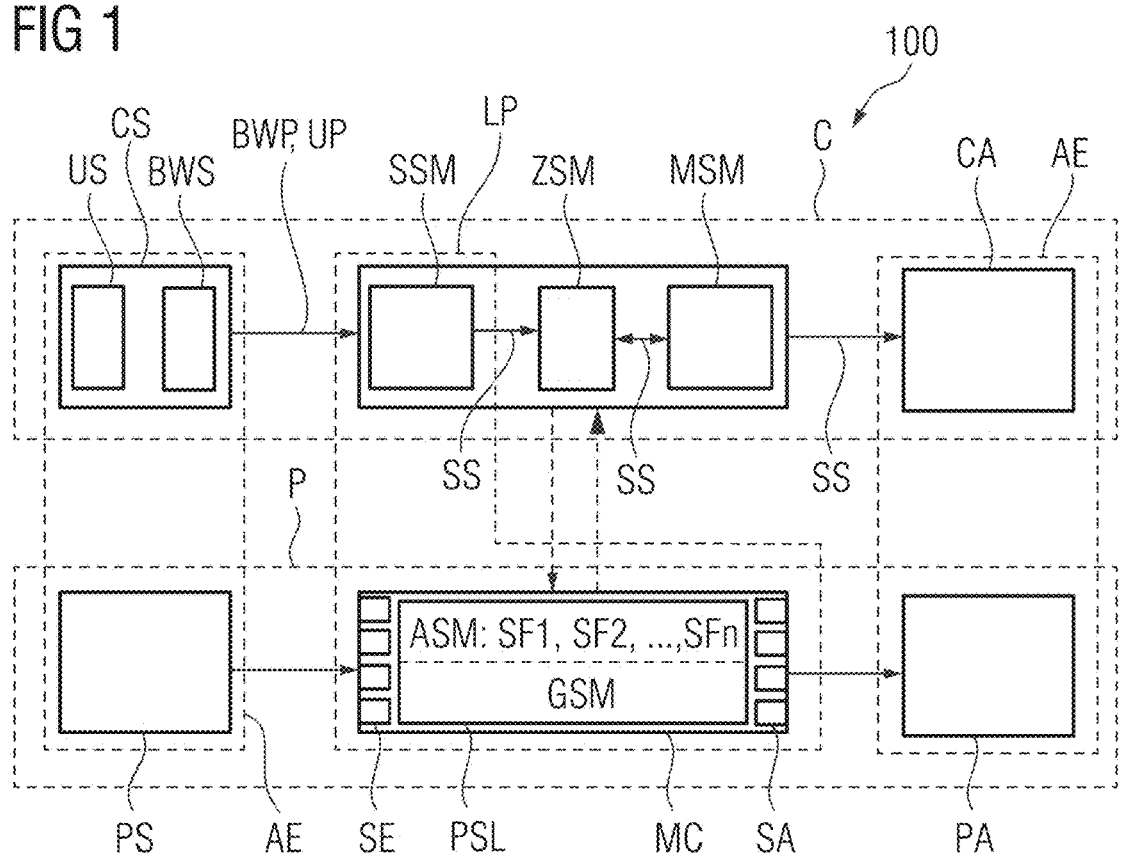
FIG. 1 a view of a control system according to one embodiment of the present invention, FIG. 2 a view of a control system according to a further embodiment of the present invention, and FIG. 3 a view of a medical installation in an embodiment comprising the control system shown in FIG. 2.

FIG. 1 shows a view of a control system 100 according to one embodiment of the present invention. The control system 100 serves to control a motorized movement of an installation component AK, for example a stand on which an imaging unit, for example an X-ray tube or an X-ray detector or the like, is mounted. The control system 100 comprises a control path C for controlling the motorized movement. The control path C forms or implements the functional part of the movement control. The control system 100 further comprises a protection path P independent of the control path. The protection path P is embodied to monitor the control path with regard to compliance with a safety criterion for the motorized movement. The control system 100 is characterized in that the protection path comprises a freely programmable microcontroller MC. The protection path P is consequently embodied to check safety-critical control functions of the control path C. The protection path P is further embodied to bring the medical installation 10 or the movable installation component AK into a safe state of movement automatically, i.e., without the intervention of a user of the medical installation, if the protection path P establishes that at least one safety criterion has been violated. For this purpose, the movement of the installation component can be stopped or slowed down; alternatively or additionally, the protection path P can trigger a reversal of the direction of movement to safeguard the state of movement.

The microcontroller MC comprises a plurality of digital and analog signal inputs SE and signal outputs SA. The signal inputs SE and the signal outputs SA are embodied as standardized analog and/or digital communication interfaces. In particular, it comprises safe communication interfaces. In particular, it can comprise a plurality of standardized sensor or actuator interfaces. FIG. 1 shows four signal inputs SE and signal outputs SA by way of example in each case. The microcontroller MC actually comprises, for example, between 50 and 100 interfaces in order to be able to acquire a plurality of different input signals or input values and form a wide variety of output interfaces to further components of the control system 100. Depending upon the type of movable installation component AK or the movement to be executed, the inputs and outputs required in each case can be selected from the plurality of signal inputs and signal outputs SE, SA without herein requiring any hardware adaptations. At least one signal input SE is linked to at least one signal output SA via programmable safety logic PSL. In fact, many of the signal inputs SE are connected to many of the signal outputs SA. The programmable safety logic PSL converts the input values into output values, which are then transmitted to other components of the protection path P and/or the control path C via the signal outputs SA within the control system 100.

The microcontroller MC or the safety logic PSL are freely programmable, i.e., there are no restrictions per se with regard to the computing operations that can be performed on the different input values. This enables even more complex functional relationships between input values and output values of the microcontroller MC to be implemented which go well beyond discrete AND/OR links. In particular, this enables speed or torque to be adapted.

The at least one safety criterion is at least one criterion from the following group:
  a minimum distance of the installation component and/or the medical installation,
  a maximum speed of movement,
  a maximum acceleration,
  maximum torque,
  maximum force,
  a position boundary along a direction of movement.

Values for the individual safety criteria are stored, for example, as threshold values specific to the movable installation component AK within the programmable safety logic PSL.

According to embodiments of the present invention, the programmable safety logic PSL comprises for each link at least one application-specific safety function SF1, SF2, ..., SFn for compliance with at least one of the above safety criteria. In other words, a safety function converts at least one input value acquired via a signal input SE via its functional relationship into at least one output value, which is output via the at least one linked signal output SA.

In this embodiment of the control system 100, the control path C comprises a central control module ZSM, a motor control module MSM and an interface module SSM.

The control path C furthermore comprises a sensor module SM, wherein the sensor module SM comprises at least one surroundings sensor US and/or a movement sensor BWS embodied in each case to acquire a surroundings parameter UP and/or a movement parameter BWP of the medical installation 10 as an input value or input signal and to transmit the same to the interface module SSM.

In addition, the sensor module SM can also comprise at least one position sensor and/or at least one operation sensor (not shown) embodied in each case to acquire a position parameter and/or an operation parameter of the medical installation 10 and likewise transmit the same to the interface module SSM. For this purpose, the sensor module SM and interface module SSM likewise comprise suitable, preferably standardized, interfaces in order to enable data exchange.

In some embodiments, the sensor module SM comprises a control sensor system CS belonging to the control system, which is embodied to provide at least one input value in the form of one of the aforementioned parameters for the control path C.

In the embodiment shown, the sensor module SM furthermore comprises a redundant protection sensor system PS comprising at least one sensor redundant to the control sensor system CS, which is embodied to acquire input values in the form of at least one surroundings parameter, movement parameter, operation parameter and/or position parameter for the protection path P or its microcontroller MC and provide the same via corresponding signal inputs SE.

The provision of a redundant protection sensor system PS and a redundant protection actuator PA enables the independence and thus the reliability of the protection path to be increased with regard to the operational safety of the medical installation 10.

If no redundant protection sensor system PS is provided in the sensor module SM, the corresponding signal inputs SE of the microcontroller MC can be connected to the control sensor system CS.

The interface module SSM of the control path C is embodied to acquire input data, i.e., a surroundings parameter UP, a movement parameter BWP, a position parameter and/or an operation parameter from the sensor module SM and, based thereon, to generate and transmit a control signal SS for the central control module ZSM and/or the motor control module MSM. The interface module SSM is in particular embodied to execute preprocessing steps, for example filtering of the input data, and to provide intermediate results.

The central control module ZSM is embodied to generate output data or output values in the form of control signals SS for a drive unit AE of the medical installation 10. Herein, the drive unit AE can comprise a control actuator CA and a protection actuator PA, in each case comprised by either the control path or the protection path. Alternatively, the drive unit AE can be embodied as belonging entirely to the control path. In this embodiment, the protection path, in particular the microcontroller MC, is embodied to communicate with the control actuator CA of the drive unit via at least one signal output SA and to transmit output values of the associated safety function. In this embodiment, no protection actuator PA redundant to the control actuator CA is provided. The control actuator CA and protection actuator PA can comprise actuators for a motorized drive that are known per se, for example an electric motor or a brake.

The control signals output by the central control module ZSM can in turn be present in the form of intermediate results, trigger signals and/or control commands. The central control module ZSM is embodied to transmit the control signals to a motor control module likewise comprised by the control path C in the form of a motor controller MSM, where they are further processed or converted. The motor controller MSM is consequently embodied to control the drive unit AE in accordance with the generated control signals SS. The motor controller MSM is therefore embodied to convert control signals received from the central control module ZSM into control commands for the drive unit.

As illustrated by the dashed arrows, the protection path P or the microcontroller MC is embodied to communicate with the control path C via at least one signal output SA and/or signal input SE of the microcontroller MC. In other words, at least one calculation result of the programmable safety logic PSL can serve as an input value for the interface module SSM, central control module ZSM and/or the motor controller MSM and be further processed by the latter in each case. Conversely, a calculation result of the control path C can function as an input value for the programmable safety logic PSL. In this respect, the control path C and protection path C collaborate with each other and exchange data bidirectionally.

As will be explained in more detail with reference to FIG. 2, in some embodiments, the interface module SSM or also the microcontroller MC is embodied to acquire a user input NE of the medical installation 10 via a data interface or a signal input SE with an input unit. The user input NE can also function as an input value of the control logic of the control path C and/or the programmable safety logic PSL of the protection path P.

In the embodiment shown here, the freely programmable microcontroller MC of the protection path P is arranged as a standalone function block on the same printed circuit board LP, a conventional printed circuit board, as the interface module SSM of the control path C. In this way, this embodiment implements a particularly simple, space-saving and inexpensive integration of the safety functionality into existing movement control hardware.

Here, the microcontroller MC or the programmable safety logic PSL further comprise a generic software module GSM and an application-specific software module ASM. The application-specific software module comprises the plurality of application-specific safety functions SF1, SF2, ..., SFn introduced above for compliance with at least one safety criterion in each case. The generic software module GSM is further embodied to enable access to the application-specific software module ASM and/or to perform application-specific safety test methods for individual signal inputs SE, signal outputs SA and/or application-specific safety functions SF1, SF2, ..., SFn.

Figure 2:
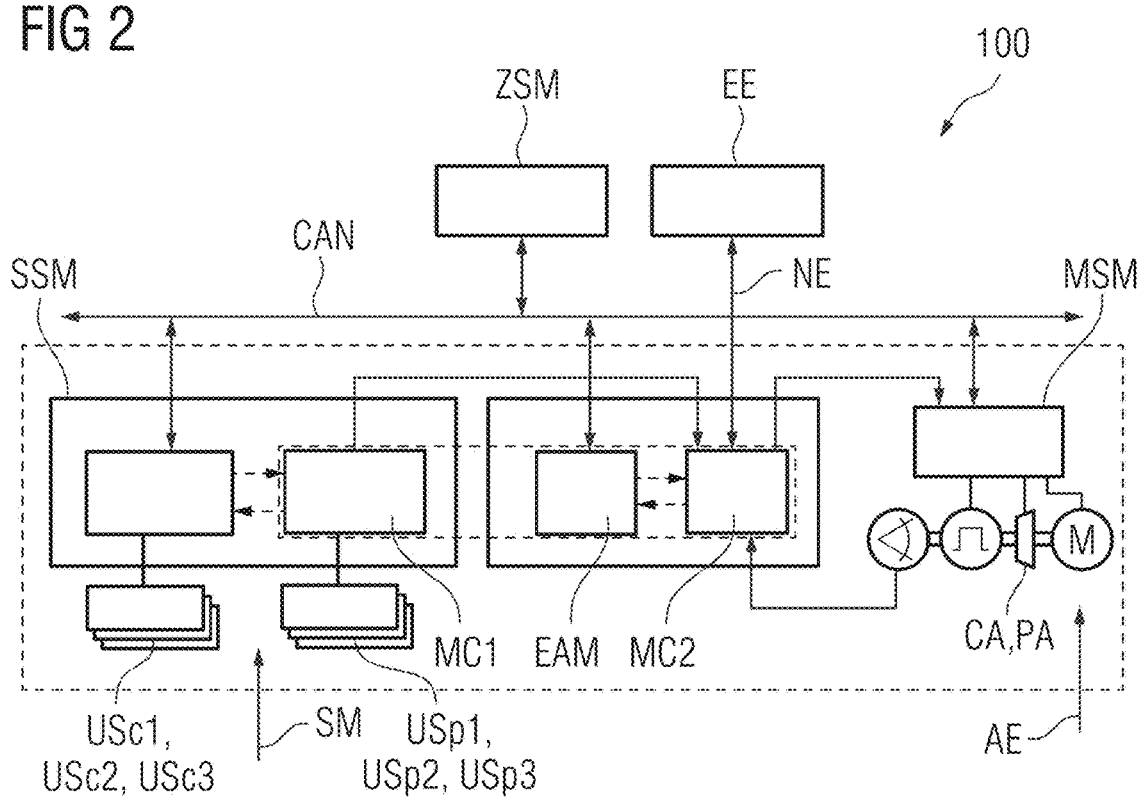
Figure 3:
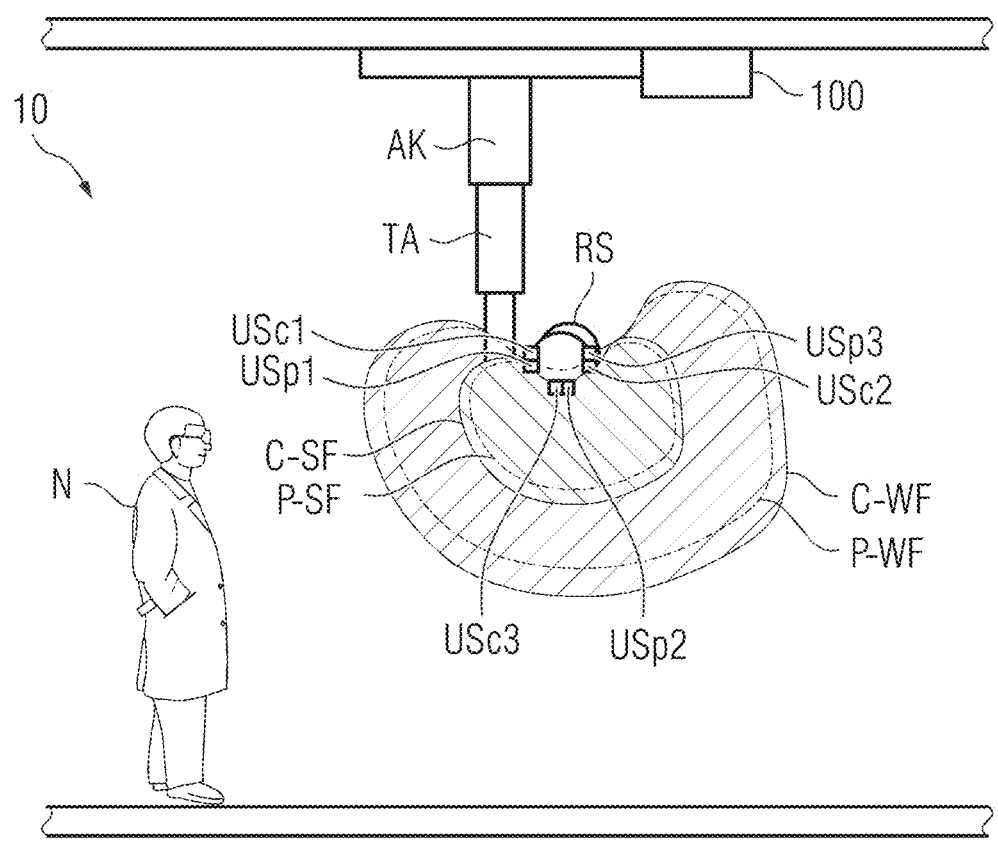

FIG. 3 shows a view of a medical installation 10 in an embodiment comprising the control system 100 shown in FIG. 2. Here, the medical installation 10 is embodied as a medical imaging installation, specifically as a radiography installation, and comprises a movable installation component AK in the form of a ceiling-mounted X-ray tube stand. Here, the ceiling-mounted X-ray tube stand can, for example, be adjusted along all three spatial directions, wherein a ceiling-mounted rail system, not shown in detail, is provided. The X-ray tube stand AK further comprises a telescopic arm TA by which the X-ray tube emitter RS can be adjusted vertically. Furthermore, it can be provided that the X-ray tube emitter RS is arranged rotatably around a horizontal axis and can be inclined or tilted accordingly.

In one embodiment of the medical installation 10, in addition to the ceiling-mounted X-ray tube stand AK, it also comprises a further movable installation component (not shown), for example in the form of a movable patient bench. An X-ray detector can be integrated into the patient bench in a detector drawer. Alternatively, a further movable installation component can be provided in the form of a further stand comprising the X-ray detector.

In a further embodiment (not shown) of the medical installation 10, it is embodied as a mobile medical X-ray imaging installation that can move freely, at least partially autonomously, in an examination setting. In this embodiment, the medical installation 10 per se forms the movable installation component AK.

An adjusting movement of the movable installation components is, for example, directed at aligning the X-ray source RS, the X-ray detector and/or the patient or a body region to be mapped or bringing the movable installation components into a rest position.

The medical installation 10 also comprises a control system 100. This is depicted in detail in a further embodiment in FIG. 2.

The X-ray tube emitter RS is surrounded by sensors of the sensor module SM of the control system 100. In detail, there are three surroundings sensors USc1, USc2 USc3 of the control path C of the control system 100 and three redundant surroundings sensors USp1, USp2, USp3 of the protection path P of the control system 100 that are embodied as proximity sensors, for example as radar sensors, and detect when an object, for example a user N or a further movable component of the medical installation 10 approaches the X-ray tube stand AK.

The surroundings sensors USc1, USc2, USc3 of the control path C monitor a control warning field C-WF and a control safety field C-SF and thus two zones around the X-ray tube stand AK. Herein, the control warning field C-WF has a larger volume than the control safety field C-SF. This embodiment of zones enables the control path C of the control system 100 to implement a control logic in which the system reacts to the approach of an object N in a stepwise manner. In the event of a violation of the control warning field C-WF, first, a speed of movement of the X-ray tube stand AK can be reduced. For this purpose, a control logic can be stored in the central control module ZSM of the control path C to ascertain whether the control warning field C-WF has been violated based on the raw sensor data or surroundings parameters of the surroundings sensors USc1, USc2, USc3 preprocessed by the interface module SSM. For this purpose, a first distance threshold value specific to the control warning field C-WF is compared with the surroundings parameters acquired. If this first distance threshold value is undershot, a control signal for the motor control module MSM is generated, which in turn controls the electric motor M of the drive unit AE. The control signal is embodied such that, for example, the motor torque is reduced and thus the speed of movement of the X-ray tube stand AK is reduced.

Furthermore, the control logic in the central control module ZSM can compare the repeatedly updated surroundings parameters of the surroundings sensors USc1, USc2, USc3 with a second distance threshold value specific to the control safety field C-SF. The second distance threshold value is smaller than the first distance threshold value. As long as one or all of the surroundings parameters lie between the first and second distance parameters, the speed of movement of the X-ray tube stand AK is regulated via the actuation of the motor control module MSM and possibly the associated control actuator CA to a predefined maximum permissible speed value. If the second distance threshold value is undershot, i.e., the control safety field C-SF is violated, the movement of the X-ray tube stand AK is automatically stopped immediately via the use of the control actuator CA, for example a motor brake, and the movable component is put into idle state.

In this embodiment, communication within the control path takes place via a CAN bus and a corresponding communication protocol.

Thus, the control system 100 according to an embodiment of the present invention implements the functional part of an autonomous device movement. However, the medical installation 10 is required to have first-failure safety even in fully autonomous operation. Therefore, the control system comprises a second protection path C independent of the control path C.

The protection path C also comprises surroundings sensors in the form of proximity sensors. The redundant surroundings sensors USc1, USc2 USc3 of the protection path P are only marginally offset from the surroundings sensors of the control path and in turn monitor a protection warning field P-WF and a protection safety field P-SF. Here, the radii, i.e., the respective distance threshold values of the protection fields, are somewhat smaller than those of the respective control fields. In other embodiments, the distance threshold values of the protection path and the control path can also be the same.

The redundant surroundings sensors now enable the control system to independently acquire distances between the movable component and an object N. The redundant surroundings parameters are now, for example, fed to a first microcontroller MC1 of the protection path P via sensor signal inputs. This microcontroller MC1 is at least partially integrated on the same printed circuit board as the interface module SSM. The programmable safety logic PSL of the first microcontroller MC1 can now be linked to a second microcontroller MC2 via at least one signal output, which is also integrated in an I/O board of the control system. This second microcontroller MC2 in turn implements a programmable safety logic PSL. This comprises at least one safety function for monitoring compliance with the aforementioned limited maximum speed of movement for the X-ray tube stand AK if the distances ascertained via the redundant surroundings sensors USc1, USc2, USc3 lie between the distance threshold values of the protection fields. Consequently, the at least one safety function checks compliance with a speed of movement for acquired object distances based on a corresponding speed threshold value. For this, a current speed of movement is repeatedly tapped via a rotary encoder via a signal input of the second microcontroller MC2 and used as an input value of the safety function.

If a current speed of movement is below the specified speed threshold value, the protection path does not react and the control path continues to regulate the speed of movement as described in the introduction. If it is detected that the speed threshold value has been overshot, the protection path ensures that the movable component AK is transferred to the safe state. For this purpose, it is provided in the present case that the second microcontroller MC2 generates a control command SS corresponding to a general safe torque off (STO) and thus controls the motor controller MSM so that the electric motor no longer transmits any force or no longer applies any torque. Alternatively and/or additionally thereto, a control signal for a motor brake can be generated so that it substantially closes instantaneously.

Here, communication between the two microcontrollers MC1 and MC2 and the motor control module MSM is implemented via digital signals.

For a non-autonomous variant of the X-ray tube stand AK, the control system 100 could dispense with the sensor module SM or the interface module and the first microcontroller MC1. A user-monitored movement via a user input NE via an input unit of the medical installation EE (DMG—dead man's grip) would thus still be possible. In this case, the input unit EE corresponds to a dead man's switch that has to be actuated or held to authorize a motorized movement. The release signal is fed via a corresponding signal input to the second microcontroller MC2 which transmits a trigger signal to an a I/O module EAM of the control path according to its programmable safety logic. As long as the release signal is received, the second microcontroller MC2 triggers the control path via the I/O module to take over the movement control according to the control logic implemented in the central control module ZSM. If the release signal is omitted because, for example, the user has released the dead man's switch, the second microcontroller MC2 generates a control signal according to a general system torque off for the motor control module MSM.

The following summarizes embodiments of the present invention once again:

The present invention relates to a control system comprising an in-house developed protection path that implements a freely programmable safety logic. In addition to standardized digital signal inputs and signal outputs, the protection path also offers communication interfaces for connecting motor rotary encoders. In this way, the protection path can also monitor dangerous or safety-critical axes of movement. In addition, the protection path further also comprises communication interfaces to a plurality of surroundings sensors or the like so that the protection path is in particular embodied to identify whether an object is approaching the movable installation component of the medical installation or vice versa.

The protection path can take over the monitoring task or a movement release that was previously the responsibility of the user of the medical installation. In general, the protection path advantageously improves the responsiveness of the control system, because the reaction time of the protection path is far superior to manual reaction on the part of the user. This also reduces the residual risk caused by the motorized movement.

The protection path according to embodiments of the present invention is embodied as a circuit macro comprising at least one microcontroller which can be integrated on any application-specific printed circuit board of existing control systems comprising a functional control path. The circuit macro provides a set of standardized data interfaces that can be connected to any sensors and actuators of the movable installation component to implement the safety functions embedded in the programmable safety logic on the microcontroller. For connection to the and interaction with the functional control path of the control system, the circuit macro provides standardized communication interfaces or uses standardized communication protocols (for example UART or SPI). These enable simple access to the circuit macro in order to be able to perform state changes, downloads, parametrization or failure diagnosis for the protection path.

The freely programmable microcontroller of the protection path executes the programmed safety logic. A watchdog in turn monitors the correct embodiment of the program code of the safety logic on the microcontroller.

Hence, the use of the generic freely programmable circuit macro within an independent protection path in combination with an application-specific control path enables easy implementation of control-protection architectures that may be recommended by a certification authority as a possible reference solution for implementing safety functions. This is because the safety-related properties of the protection path according to embodiments of the present invention can be described independently of the application.

The use of the circuit macro according to embodiments of the present invention to implement safety functions significantly reduces expenditure for development and authorization for the respective applications. The material costs for the circuit macro are only composed of the component costs and the required circuit board area. These are significantly lower than the costs for comparable industrial solutions. The circuit macro offers very high flexibility together with low material costs. The wide range of applications reduces initial development and approval costs.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where not yet explicitly done, but useful and in the spirit of the present invention, individual embodiments, individual aspects or features thereof may be combined or interchanged without leaving the scope of the present invention. Where transferable, advantages of the present invention described with reference to one embodiment also apply to other embodiments without explicit mention.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A control system for a medical installation, the control system configured to control a motorized movement of an installation component, the control system comprising:
   a control path configured to control the motorized movement; and
   a protection path independent of the control path, wherein
      the protection path is configured to monitor the control path with regard to compliance with a safety criterion for the motorized movement, and
      the protection path includes at least one freely programmable microcontroller.

2. The control system as claimed in claim 1, wherein the at least one freely programmable microcontroller comprises a plurality of digital and analog signal inputs and signal outputs, wherein at least one signal input is linked to at least one signal output via programmable safety logic.

3. The control system as claimed in claim 2, wherein the programmable safety logic comprises at least one application-specific safety function for each link for compliance with a safety criterion.

4. The control system as claimed in claim 1, wherein the control path comprises:
   a central control module configured to generate control signals for a drive unit of the medical installation;
   a motor control module configured to control the drive unit according to the control signals; and
   an interface module configured to
      acquire at least one of a surroundings parameter, a movement parameter or a user input of the medical installation, and
      generate and transmit a control signal based on the at least one of the surroundings parameter, the movement parameter or the user input of the medical installation, the control signal being for at least one of the central control module or the motor control module.

5. The control system as claimed in claim 4, wherein the control path further comprises a sensor module, wherein the sensor module includes at least one of at least one surroundings sensor or a movement sensor, the at least one surroundings sensor configured to obtain the surroundings parameter and transmit the surroundings parameter to the interface module, and the movement sensor configured to obtain the movement parameter and transmit the movement parameter to the interface module.

6. The control system as claimed in claim 1, wherein the at least one freely programmable microcontroller is configured as a standalone function block on a same printed circuit board as an interface module of the control path.

7. The control system as claimed in claim 2, wherein the protection path is configured to communicate with the control path via at least one of at least one signal output or at least one signal input of the at least one freely programmable microcontroller.

8. The control system as claimed in claim 1, wherein the at least one freely programmable microcontroller comprises:
   an application-specific software module including a plurality of application-specific safety functions for compliance with at least one safety criterion in each case; and
   a generic software module configured to at least one of enable access to the application-specific software module or perform application-specific safety test methods for at least one of individual signal inputs, signal outputs or application-specific safety functions.

9. The control system as claimed in claim 5, wherein the protection path comprises:
   at least one of at least one redundant surroundings sensor or at least one further movement sensor, the at least one redundant surroundings sensor configured to obtain the surroundings parameter and transmit the surroundings parameter to the at least one freely programmable microcontroller, and the at least one further movement sensor configured to obtain the movement parameter and transmit the movement parameter to the at least one freely programmable microcontroller.

10. The control system as claimed in claim 2, wherein at least one signal input of the at least one freely programmable microcontroller is connected to an input unit of the medical installation to acquire a user input redundantly to the control path.

11. The control system as claimed in claim 1, wherein the safety criterion is at least one of:
   a minimum distance of at least one of the installation component or the medical installation,
   a maximum speed of movement,
   a maximum acceleration,
   maximum torque,
   maximum force, or
   a position boundary along a direction of movement.

12. A medical installation comprising:
   the control system as claimed in claim 1, the control system configured to control the motorized movement of the installation component.

13. The medical installation as claimed in claim 12, wherein the medical installation is a radiography installation including two movable installation components in the form of an X-ray tube stand and a patient bench.

14. The medical installation as claimed in claim 12, wherein the medical installation is a mobile medical X-ray imaging installation.

15. The control system as claimed in claim 2, wherein the control path comprises:
   a central control module configured to generate control signals for a drive unit of the medical installation;
   a motor control module configured to control the drive unit according to the control signals; and
   an interface module configured to
      acquire at least one of a surroundings parameter, a movement parameter or a user input of the medical installation, and
      generate and transmit a control signal based on the at least one of the surroundings parameter, the movement parameter or the user input of the medical installation, the control signal being for at least one of the central control module or the motor control module.

16. The control system as claimed in claim 15, wherein the at least one freely programmable microcontroller comprises:
   an application-specific software module including a plurality of application-specific safety functions for compliance with at least one safety criterion in each case; and
   a generic software module configured to at least one of enable access to the application-specific software module or perform application-specific safety test methods for at least one of individual signal inputs, signal outputs or application-specific safety functions.

17. The control system as claimed in claim 4, wherein the at least one freely programmable microcontroller comprises:
- an application-specific software module including a plurality of application-specific safety functions for compliance with at least one safety criterion in each case; and
- a generic software module configured to at least one of enable access to the application-specific software module or perform application-specific safety test methods for at least one of individual signal inputs, signal outputs or application-specific safety functions.

18. The control system as claimed in claim 17, wherein the protection path comprises:
- at least one of at least one redundant surroundings sensor or at least one further movement sensor, the at least one redundant surroundings sensor configured to obtain the surroundings parameter and transmit the surroundings parameter to the at least one freely programmable microcontroller, and the at least one further movement sensor configured to obtain the movement parameter and transmit the movement parameter to the at least one freely programmable microcontroller.

19. The control system as claimed in claim 8, wherein the protection path comprises:
- at least one of at least one redundant surroundings sensor or at least one further movement sensor, the at least one redundant surroundings sensor configured to obtain a surroundings parameter and transmit the surroundings parameter to the at least one freely programmable microcontroller, and the at least one further movement sensor configured to obtain a movement parameter and transmit the movement parameter to the at least one freely programmable microcontroller.

20. The control system as claimed in claim 4, wherein at least one signal input of the at least one freely programmable microcontroller is connected to an input unit of the medical installation to acquire a user input redundantly to the control path.

* * * * *